United States Patent [19]

Khan et al.

[11] 4,177,254

[45] Dec. 4, 1979

[54] ORALLY ADMINISTRABLE PHARMACEUTICAL COMPOSITION

[75] Inventors: Karrar A. Khan, Worthing; Brian Cook, Goring-by-Sea, both of England

[73] Assignee: Beecham Group Limited, England

[21] Appl. No.: 923,933

[22] Filed: Jul. 13, 1978

Related U.S. Application Data

[63] Continuation of Ser. No. 750,609, Dec. 15, 1975, abandoned.

[30] Foreign Application Priority Data

Jan. 2, 1976 [GB] United Kingdom ............... 00023/76

[51] Int. Cl.$^2$ .......................... A61K 9/16; A61K 9/36; A61K 31/43
[52] U.S. Cl. ....................................... 424/16; 424/35; 424/27; 424/361; 427/3; 264/209
[58] Field of Search ...................... 424/141.6, 35, 271, 424/361; 427/3; 264/209

[56] References Cited

U.S. PATENT DOCUMENTS

| | | | |
|---|---|---|---|
| 2,811,483 | 10/1957 | Aterno et al. ...................... | 424/35 X |
| 2,953,497 | 9/1960 | Press .................................. | 424/35 X |
| 2,996,431 | 8/1961 | Barry .................................. | 424/35 X |
| 3,079,303 | 2/1963 | Raff et al. .......................... | 424/35 X |
| 3,081,233 | 3/1963 | Enz et al. ........................... | 424/35 X |
| 3,089,824 | 5/1963 | Wurster ............................. | 424/35 X |
| 3,619,294 | 11/1971 | Black et al. ........................ | 424/361 X |
| 3,639,169 | 2/1972 | Broeg et al. ....................... | 424/361 X |
| 3,932,615 | 1/1976 | Ito et al. ........................... | 424/361 X |
| 3,951,953 | 4/1976 | Khan .................................. | 424/271 X |
| 4,016,254 | 4/1977 | Seager ................................ | 424/33 |

*Primary Examiner*—Shep K. Rose
*Attorney, Agent, or Firm*—Jacobs & Jacobs

[57] ABSTRACT

Two, preferably three, layered orally administrable granules containing orally administrable penicillins have desirable properties such as elegance, freedom from dust and good reconstitution. They contain an inert core, preferably of sucrose, a penicillin/binder first layer and normally and preferably a final coating layer of conventional additives such as dyes, flavors etc..

Preferably the penicillin is amoxycillin trihydrate and the binder sucrose. The granules may be prepared by fluid bed granulation.

15 Claims, No Drawings

ORALLY ADMINISTRABLE PHARMACEUTICAL COMPOSITION

CROSS-REFERENCE

This is a continuation of Ser. No. 750,609, filed Dec. 15, 1976, now abandoned.

This invention relates to orally administrable pharmaceutical granules, to a process for their preparation, and to a method for their use.

It is known to formulate penicillins into granules for oral administration purposes. These granules may be taken by the patient either in the dry form or reconstituted into a syrup. Such granules can have advantages over powders, for example, in flow properties and in a relative freedom from dust, and also are often preferred by the consumer for purely cosmetic reasons.

Conventional methods for preparing such granules include, in outline, mixing a penicillin with a solution of a binder until a suitable granulating consistency is achieved, force seiving this mix through a seive of the desired mesh size, and then drying the resultant granules. A known technique which gives granules of a generally better quality than the afore-described 'wet mix' granulation method is fluid bed granulation. In this technique, a solution of a binder is sprayed on to a fluidised penicillin on the reactor bed.

We have now discovered a class of granules having beneficial properties, for example, excellent reconstitution and stability properties. We have also discovered a particularly useful process for the preparation of these granules involving a novel application of a fluid bed granulator. This process has a number of advantages, such as allowing the size of the granules prepared thereby to be controlled within a narrow diameter range, and results in the granules prepared thereby being relatively free of dust.

Accordingly the present invention provides orally administrable granules, which granules comprise a particle or agglomerate of particles; the particle or particles comprise a core which core comprises a sugar, mannitol or sorbitol, and a coating layer which coating layer comprises a penicillin and a binder.

Preferably in these granules the cores comprise sucrose.

Particularly useful granules according to the invention comprise a particle or agglomerate of particles; the particle or particles comprise a core which core comprises a sugar, mannitol or sorbitol, and a coating layer which coating layer comprises a penicillin and a binder; and the particle or agglomerate of particles is coated with conventional granule additives.

Preferably in these granules the cores comprise sucrose.

The term 'additive' used herein means any substance conventionally added to granules in pharmaceutical formulation to improve the quality or appearance of the granules, or of syrups formed therefrom. Examples of such additives include binders, lubricants, flavours, colours, disintegrants, dyes, anti-foaming agents and the like. The provision of a layer of such additives in the granules of the invention is not essential but is very much preferred because it allows the properties of the granules to be optimised. For example the taste, flowability, elegance and reconstitution properties of the granules may be improved in this way.

The core of the granules comprises a sugar, mannitol or sorbitol. Examples of suitable sugars for this use include sucrose, glucose, fructose and lactose, and mixtures thereof. Suitably the core material will be in crystalline form.

Sucrose is the preferred material for the core of the granules, due to its pleasant taste and relative cheapness. When used, it will normally represent 80%, preferably substantially 100% of the core of the granules. Suitably the sucrose is sucrose B.P.

The coating layer around the core of the granules comprises a penicillin and a binder, the binder being necessary to retain the penicillin in this 'shell' around the core.

The penicillin may be any penicillin or mixture of penicillins that is absorbed from the gastrointestinal tract after oral administration. Due to the mode of administration of the granules, it is preferred that the penicillin is palatable or at least of a neutral taste. However, a less pleasant tasting penicillin may be used if its specific mode and spectrum of activity is required. In such cases flavour additives will normally be incorporated into the granules. Examples of penicillins that may suitably be used in the granules include the following semi-synthetic penicillins: ampicillin, ampicillin trihydrate, and amoxycillin trihydrate. Other examples include the following semi-synthetic penicillins in the form of a salt of sufficiently poor solubility in water to be of acceptable taste: orally absorbable esters of ampicillin and amoxycillin, such as the phthalidyl ester and the pivaloyl oxymethyl ester e.g. the phthalidyl ester of ampicillin; cloxacillin, dicloxacillin, flucloxacillin, oxacillin; and orally absorbable esters of carbenicillin and ticarcillin, such as the phenyl, indanyl and tolyl α-esters. Ampicillin, ampicillin trihydrate and amoxycillin trihydrate are particularly suitable penicillins for incorporation into the granules, and of these two amoxycillin trihydrate is often the penicillin of choice.

The binder may be any of the conventional binders used in pharmaceutical formulation. Examples of such binders include polymeric binders, for example cellulose polymers such as methyl and ethyl cellulose, hydroxymethyl cellulose, sodium carboxymethyl cellulose and the like; other synthetic polymers such as polyvinylpyrrolidone and the like; and natural gums and resins such as gelatin, acacia, carragheen, alginic acid, tragacanth, gum arabic and the like. Starch and sucrose and the like may also be used.

Preferably however the binder is water soluble so that on reconstitution the resultant granules readily yield a suspension of their active ingredient. Examples of such binders include polymeric binders, for example cellulose polymers such as methylcellulose, sodium carboxy methyl cellulose, hydroxypropyl cellulose and the like; other synthetic polymers such as polyvinylpyrrolidone and the like; natural gums and resins such as gelatin, acacia and the like; starch, and sucrose. In general it is preferred that the binder is sucrose.

The coating layer will either comprise an essentially homogeneous mixture of penicillin and binder, or will comprise particles of penicillin dispersed throughout the binder.

The granules comprise a particle or agglomerate of particles as defined. Normally the granules will be of a size such that they comprise an agglomerate of particles, the particles in the said agglomerate being held in place by a coalescence of their coating layers. In such agglomerates of particles, the agglomerates will comprise a number of cores separated one from another, and coated by, the coating layer comprising penicillin and binder. As explained, the particle or agglomerate of particles making up each granule is preferably coated with conventional granule additives.

The size of the granules is essentially a matter of choice, bearing in mind factors such as the nature of the use to which the granules are to be put. Normally the size of the granules will be in the range 180μ to 1400μ more suitably 250μ to 700μ.

The essential ingredients of the granules are a sugar, mannitol or sorbitol; a penicillin; and a binder. Additives will normally also be present as described.

The penicillin will normally represent on average between 1 and 20% by weight of each granule, suitably 3 to 18%, more suitably 3 to 12%.

The binder must be present in a sufficient weight so as to serve its function of holding the penicillin in place in the layer of penicillin and binder around the particle cores. While this function can sometimes be effected by an interaction between the penicillin and the surface of the particle cores when the cores are sucrose (in which case the weight of the binder-sucrose- in the coating layer will of course be extremely small), normally and preferably the binder will be present in more substantial quantities. For example when the binder is sucrose it may represent 5 to 70%, suitably 10 to 50% of the granule, the high upper limit being possible due to the pharmaceutical and cosmetic acceptability of sucrose. More suitably a sucrose binder will represent 20 to 40% by weight of the granule, for example approximately 30%. When the binder is one of the polymeric binders described earlier in the specification, or of that type, then the binder will normally represent only 1 to 15%, suitably 5 to 10% of the granule. This is because such binders are normally more efficient than a sucrose binder and thus can be used at a lower inclusion rate, but suffer from the disadvantage over sucrose that their presence in large quantities in the granules is undesirable, for example, due to their effect on a reconstituted product. As stated hereinbefore, if binders other than sucrose are used, it is preferred that they are water soluble.

The particle cores of the granules will normally represent 30 to 95%, more suitably 50 to 90%, of each granule. Obviously in general the lower percentages will be associated with the use of a sucrose binder, and the higher percentages with the use of polymeric binders. More specifically, with a sucrose binder these figures will often be 30-90% preferably 40-75%, and with polymeric binders 55-95%, preferably 70-90%. As stated hereinbefore, very much the preferred core material is sucrose.

The additives when present in a further coating layer, as they normally will be, will represent on average 1-10%, more suitably 2-6%, of each granule.

From the aforesaid it may be seen that particularly suitable granules according to the invention comprise a particle or agglomerate of particles; the particle or particles comprise a core, which core consists essentially of sucrose, and a coating layer which coating layer comprises ampicillin, ampicillin trihydrate or amoxycillin trihydrate and a binder; and the particle or agglomerate of particles is coated with conventional granule additives.

When the binder is sucrose, the preferred binder, then the core sucrose will preferably represent 40-75% by weight of the granules, and the binder sucrose 20-40% by weight of the granules. When the binder is a polymeric binder as described, the respective figures will preferably be 70-90% and 1-15%.

Amoxycillin trihydrate is the penicillin of choice for use in the granules for its combination of good oral absorption and pleasant taste.

The additives will usually comprise flavours, dyes and the like.

The present invention also provides a process for the preparation of the granules of the invention which granules do not contain the preferred coating layer of conventional additives, which process comprises coating particulate sugar, mannitol or sorbitol with a solution or suspension of a penicillin in a solution of a binder, and drying the resultant particles and/or agglomerates of particles. Preferably the coated material is sucrose.

The granules of the invention which do contain the preferred coating layer of conventional additives may be prepared by a process which comprises coating particles and/or agglomerates of particles with conventional granule additives; the said particles comprising a core which core comprises a sugar, mannitol or sorbitol, and a coating layer which coating layer comprises a penicillin and a binder. These granules are normally however prepared in a continuous process which combines the preparation of the particles and/or agglomerates of particles with their coating with additives. Such a combined process may comprise coating particulate sugar, mannitol or sorbitol with a solution or suspension of a penicillin in a solution of a binder, drying the resultant particles and/or agglomerates of particles, coating these particles and/or agglomerates of particles with conventional granule additives, and if necessary drying the resultant granules. Of the sugar, mannitol or sorbitol for use in this process, sucrose is the preferred material.

The solvent used to dissolve the binder may be any pharmaceutically acceptable inert solvent for the binder which is sufficiently volatile to be readily removed from the particles in the drying step. Examples of such solvents include water, methanol, ethanol, n- and iso-propanol, chloroform, methylene chloride, acetone, methylethylketone, methyl acetate, ethyl acetate, trichloroethylene, tetrachloroethylene, carbon tetrachloride or like solvents or homogeneous mixtures of such solvents. Water is normally the solvent of choice due to its ready availability, and because organic solvents have to be carefully collected when vaporised in the drying step. Of course when the binder is sucrose, it will be realised that syrup, or syrup diluted with water, will make a very convenient coating medium for the penicillin.

The penicillin may be soluble or insoluble in the binder solution. When it is soluble, then the resultant coating layer about the particulate cores will comprise a substantially homogeneous mixture of penicillin and binder. In the same way, when it is insoluble, then the resultant coating layer about the particulate cores will comprise particles of penicillin dispersed throughout the binder. In general it has been found that granules of higher quality are formed when the penicillin is insoluble in the binder solution, as often in this case the drying step to remove the binder solvent can be carried out at a lower temperature.

The coating of the particulate sugar, mannitol or sorbitol with the solution or suspension of the penicillin in the solution of the binder may be carried out simply by mixing the particulate material with the penicillin solution or suspension. However more normally the penicillin solution or suspension will be sprayed onto the particulate material, which material is agitated to allow a substantially uniform coating to be applied. The resultant particles and/or agglomerate of particles can then be dried in the usual way.

The coating of the particles and/or agglomerates of particles with the preferred layer of additives may similarly be carried out by simply mixing the particles and/or agglomerates of particles with the additives, particularly if the surfaces of the particles and/or agglomerates carry some residual moisture to assist the binding of the additives. However more normally the particles and/or agglomerates of particles will be sprayed with a solution of the additives in a solvent, the particles and/or agglomerates of particles being agitated to allow a substantially uniform coating to be applied. Often one of the additives will be a binder to assist in the retention of the other additives on the particles and/or agglomerates. The wet granules may then be dried in the usual way. In a variation of this process one or more additives are mixed with the particles and/or agglomerates of particles, and then this mixture is sprayed with a solvent or a solution of one or more other additives in the manner described above.

The combined process, namely the preparation of the particles and/or agglomerates of particles, and the coating thereof with additives, may be carried out by any of the methods described hereinbefore. However it has been found that one particular technique may be used which is particularly suitably to this combined process, namely fluid bed granulation. This technique is well known in the art, but in our process instead of the penicillin being spread on the bed, being fluidised and then sprayed with a binder solution as is conventional, the penicillin in a solution of the binder is sprayed onto particulate core material, it being this core material which is fluidised on the bed, not the penicillin.

Thus the present invention provides a preferred process for the preparation of the granules of the invention, which process comprises distributing particulate sugar, mannitol or sorbitol on the bed of a fluid bed granulator, fluidising this material, spraying a penicillin dissolved or dispersed in a solution of a binder onto the fluidised material, allowing the resultant particles and/or agglomerates of particles to dry, and then coating the particles and/or agglomerates of particles with conventional granule additives, and if necessary allowing the resultant granules to dry. In this process the fluidised material is preferably sucrose.

The coating of the particles with the conventional granule additives is carried out either by mixing one or more of the additives with the particles and/or agglomerates of particles, and then spraying the fluidised mixture with a solvent or a solution of one or more other additives; or by spraying the fluidised particles and/or agglomerates of the particles with a solution of all the additives. As stated earlier, often a binder will be included in the spraying solution to assist the binding of the other additives to the particles and/or agglomerates of particles.

The spraying operations may be intermittent to allow time for the partially coated materials on the bed to dry before further coating.

The operation of the fluid bed granulator in this process is as conventional, and the skilled man will readily understand how by routine variation of the granulator parameters, such as inlet air setting, inlet air temperature, outlet air setting, air pressure for pulverisation, air pressure for operation and spraying nozzle setting, the nature of the resultant granules may be varied within the confines of the invention.

After the preparation of the granules by any of the hereinbefore described processes, the granules will normally be seived to remove any granules present of undesirable proportions.

Lastly, it should be pointed out that granules have been described earlier in the specification wherein a sucrose binder is present in extremely small quantities in the penicillin/binder layer and is in fact derived from core sucrose. These granules may be prepared as described for the more suitable granules wherein the binder is present in appreciable quantities, except that particulate sucrose is coated with a solution or suspension of the penicillin in a solvent with no binder present in this solution or suspension. In this case the solvent acts to dissolve very minor proportions of the particulate sucrose which can then act as a weak binder.

The granules may be administered orally either in the dry form, or as a reconstituted syrup. The syrup may be formed from the granules in the usual way, for example by agitating the granules in a suitable solvent, such as water, together with conventional syrup additives if so desired. The composition may be presented for example in bottles or similar containers containing multiple doses, or in single dose sachets.

The weight of granules in a single dose will depend on factors such as the particular penicillin used, the percentage inclusion of the penicillin, and the nature of the malady being treated, and will be a weight suitable for the intended mode of administration. Normally, for example, between 0.5–10 g more suitable 1–5 g. of the granules will comprise a single dose.

The weight of penicillin in a single dose of the granules will be such that the single dose contains sufficient penicillin for effective treatment of the malady. The single dose will be repeated according to the usual dosage regime for the penicillin.

It may be desired to include granules containing different penicillins in a single dose of the composition in the simultaneous treatment of two or more maladies. This of course may simply be achieved for example by mixing together sufficient granules containing one penicillin with sufficient granules containing a second penicillin.

The invention also provides a method of treatment of bacterial infections in man, which method comprises the oral administration to the sufferer of an effective amount of a penicillin in the form of the granules of the invention.

The following Examples illustrate the invention.

EXAMPLE 1

16 kg. of granules of the following composition were prepared:

|  | % |
| --- | --- |
| Dry flavours | 4.2 |
| Sodium Benzoate B.P. | 0.2 |
| Sodium Citrate, anhydrous | 0.7 |
| Dye | q.s. |
| Amoxycillin trihydrate | 11.3 |
| (equivalent to 10% amoxycillin free acid) | |
| | Sucrose to 100.0 |

1. Preparation of Dye-Flavour Premix

|  | kg |
|---|---|
| Dry flavours | 6.7 |
| Sodium Benzoate B.P. | 0.3 |
| Sodium Citrate, anhydrous | 1.1 |
| Dye | q.s. |
|  | 8.1 |

The sodium benzoate and anhydrous sodium citrate were loaded into the bowl of a planetary mixer. The dye was dispersed over the surface of the materials in the bowl, and the materials mixed for 10 minutes. The resultant mix was passed through a comminuting mill to give Mix A.

The dry flavours were seived, and then loaded with Mix A into the bowl of a planetary mixer and mixed for 10 minutes, and the resultant mix stored in suitable sealed containers.

2. Preparation of Amoxycillin Trihydrate Suspension

|  |  | Dry wt. kg. |
|---|---|---|
| Amoxycillin trihydrate | 1.8 kg. | 1.8 |
| Purified water B.P. | 0.8 kg. | — |
| Syrup B.P. | 7.6 kg. | 5.1 |
|  | 10.2 kg. | 6.9 |

The syrup and 400 g. of the purified water were poured into the bowl of a suitable mixer. The amoxycillin trihydrate was added to the solution in the mixer and mixed with a paddle stirrer until a homogeneous suspension was obtained.

The suspension was passed through a colloid mill, the mill was then rinsed with 400 g. of purified water and the rinse added to the suspension.

The suspension was used immediately in operation 3.

3. Preparation of Granules

|  | kg | Dry wt. kg. |
|---|---|---|
| Dye-Flavour Premix (From 1.) | 0.8 | 0.8 |
| Amoxycillin Suspension (From 2.) | 10.2 | 6.9 |
| Sucrose | 8.3 | 8.3 |
|  |  | 16.0 |

A Glatt W.S.G. 15 Fluidised Bed Spray Granulating Machine [Glatt A.G. Halthingen, Germany] was set to the following working conditions.

| Inlet air setting | — | 7 |
|---|---|---|
| Inlet air temperature | °C. | 80 |
| Outlet air setting | — | 4 |
| Air for pulverisation | p.s.i. | 40 (or 2.5 kp/cm$^2$) |
| Air for operation | kp/cm$^2$ | 5.5–6.0 |
| Nozzle setting |  | position 4 |

The sucrose was added to the preheated Glatt and heated to 60° C. over 20 minutes. The amoxycillin trihydrate suspension was sprayed intermittently into the coating chamber. The spraying was ceased when the centre of the bed started to become overwet, and the bed allowed to dry. The spraying was resumed and the procedure repeated until all the suspension had been consumed. Small adjustments in steps in spraying rate were made to the metering pump in order to optimise the spraying and drying time.

The suspension container was rinsed with 400 ml. of purified water and the rinse sprayed into the chamber. When the bed ceased to be fluid, the spraying was ceased, the sock shaked for 10 seconds, and sufficient drying time was allowed for the bed to refluidise. The spraying was resumed and the procedure repeated until all the rinse had been consumed. Small adjustments were made to the spraying rate in order to optimise the spraying time.

60 Seconds were allowed for the thus formed particles and agglomerates of particles to dry, and the machine was then stopped. The dye/flavour premix was then added to the particles and agglomerates of particles in the coating chamber, and mixed manually. The machine was then closed and set in motion for 60 seconds to complete the mixing operation.

1200 ml. of Purified Water B.P. was then sprayed in using the same procedure as previously described. The suspension container was then rinsed with 400 ml. of purified water and the rinse sprayed into the Glatt using the same procedure as previously described.

The resultant granules were then dried in the Glatt until the moisture content was not more than 2% by Karl Fischer (approximately 20 minutes), passed through a 12 mesh 1.40 mm. stainless steel screen and any residual material discarded.

The granules were stored in suitable sealed containers.

EXAMPLE 2

Example 1 was repeated but using half the weight of amoxycillin trihydrate to yield granules containing 5% by weight of amoxycillin as the free acid.

This weight loss was made up by increasing the weight of sucrose used in operation 3 by the corresponding amount.

EXAMPLE 3

Ampicillin trihydrate (1.99 kg) was used in the place of amoxycillin trihydrate in Example 1 to yield granules containing 10% by weight of ampicillin as the free acid.

The mirror weight gain caused by this replacement was balanced by decreasing the weight of sucrose used in operation 3 by the corresponding amount.

EXAMPLE 4

Example 3 was repeated but half the weight of ampicillin trihydrate was used to yield granules containing 5% by weight of ampicillin as the free acid.

The weight loss was made up by increasing the weight of sucrose used in operation 3 by the corresponding amount.

EXAMPLE 5

The granules of Example 1, 2, 3 and 4 were found to retain their physical and pharmaceutical properties at temperatures below 30° C. for periods of at least 12 months.

EXAMPLE 6

80 kg. of granules of the composition set out in Example 1 were prepared in the following manner.
Operation 1 of Example 1 was repeated.
Operation 2

Preparation of amoxycillin trihydrate suspension

|  | kg |
|---|---|
| Amoxycillin trihydrate | 9.0 |
| Sucrose | 26.1 |
| Purified Water | 18.0 |
|  | 53.1 |

The sucrose was dissolved in the water, using a suitable container and mixer. The amoxycillin trihydrate was added to the solution and mixed until a homogeneous suspension was obtained.

The suspension was passed through a water coated colloid mill, the mill was rinsed with 3 kg of water and the rinse added to the suspension. The suspension was used immediately in Operation 3.

Operation 3

|  | kg | Dry wt. kg. |
|---|---|---|
| Dye-Flavour Premix (from 1) | 4.0 | 4.0 |
| Amoxycilli Suspension (from 2) | 53.1 | 35.1 |
| Sucrose | 40.9 | 40.9 |
|  |  | 80.0 |

An Aeromatic Strea W S. 3-30 [Aeromatic AG, Farnsburger Strasse 6, CH-4132 Muttenz, Switzerland] was set to the following working conditions.

| Inlet air temperature setting | °C. 78 |
|---|---|
| Outlet air setting | kg/cm$^{-2}$ 1.1 |
| Atomisation air pressure | kg/cm$^{-2}$ 3.6–4.0 |
| Nozzle Height | position −1.0 (minus 1.0) |

The sucrose was added and preheated to 60° C.

The amoxycillin was sprayed into the chamber onto the fluidised sucrose using a suitable pumping rate.

When approximately half the suspension had been used, the nozzle height was increased to 0 and spraying continued.

The container was then rinsed with 0.5 kg of water and the rinse was sprayed on at reduced pump speed.

The machine was stopped and the dye/flavour premix added by hand.

The machine was then set to the following conditions.

| Inlet air temperature setting | °C. 78 |
|---|---|
| Outlet air setting | kg/cm$^{-2}$ 1.0 |
| Atomisation air pressure | kg/cm$^{-2}$ 3.6–4.0 |
| Nozzle Height | position +1.5 |

The machine was set in motion and allowed to mix for 1 minute. 7 kg of water was used to rinse the container and metered onto the fluidised materials at 40 Umm$^{-1}$. The resultant granules were dried in the Aeromatic for approximately 20 minutes to less than 2% moisture content by Karl Fischer. The granules were passed through a 12 mesh (1.40 mm) stainless steel screen and any residual material discarded.

The granules were stored in suitable sealed containers.

TOXICITY

The granules prepared in these Examples were found to be of similar acceptability to their active ingredient.

What we claim is:

1. A process for the preparation of water-soluble or water-dispersible granules of water-insoluble penicillins, said granules being reconstitutable to syrup form, which comprises coating particulate sugar, mannitol or sorbitol with a suspension of the water-insoluble penicillin in a sucrose solution binder, and drying the resultant particles or agglomerates of particles, the process being carried out by fluid bed granulation using water as solvent for the binder.

2. A process according to claim 1, wherein the coating of the particles or agglomerated particles is carried out with known granule additives and the process is carried out by fluid bed granulation using water as a solvent for the sucrose binder.

3. A process according to claim 2, which comprises coating sucrose with a suspension of the water-insoluble penicillin in an aqueous solution of the binder, drying the resultant particles or agglomerated particles, and then coating these particles or agglomerated particles with the granule additives, the process being carried out by fluid bed granulation using water as solvent for the sucrose binder.

4. A process according to claim 1, which comprises coating particulate core sucrose with a suspension of ampicillin, ampicillin trihydrate or amoxycillin trihydrate in a solution of the sucrose binder, and drying the resultant particles or agglomerated particles, the process being carried out by fluid bed granulation using water as a solvent for the sucrose binder.

5. A process according to claim 4, which comprises coating particulate sucrose with a suspension of the amoxycillin trihydrate in a water solution of the sucrose binder, drying the resultant particles or agglomerated particles, and then coating these particles or agglomerated particles with known granule additives.

6. An orally administrable pharmaceutical composition produced by a fluid bed granulation process in accordance with claim 1, consisting essentially of layered granules exteriorly coated with additives and having a core of a sugar, mannitol or sorbitol coated with a water-insoluble penicillin dispersed in sucrose as binder, said granules being water-soluble or water-dispersible.

7. A composition according to claim 6 wherein the granules are made up of particles or agglomerated particles in which the core is sucrose.

8. A composition according to claim 7 wherein the granule coating additives are conventional and are water-soluble or water-dispersible to form water-soluble or water-dispersible granules useful in granule form or re-constitutable to syrup form.

9. A composition according to claim 8 wherein the sucrose cores constitute 70–95% of the granules.

10. A composition according to claim 6 wherein the penicillin is ampicillin, ampicillin trihydrate, or amoxycillin trihydrate.

11. A composition according to claim 6 wherein the penicillin is amoxycillin trihydrate.

12. A composition according to claim 6 wherein the sucrose binder constitutes 1–15% of the granules.

13. A composition according to claim 8 wherein the additives constitute 1–10% of the granules.

14. A composition according to claim 8 wherein the additives constitute 1–10% of the granules and are selected from binders, lubricants, flavors, colors, disintegrants, dyes and anti-foaming agents.

15. A composition according to claim 9 wherein the core sucrose constitutes 30–95% and the binder sucrose constitutes 1–15% of the granules.

* * * * *